(12) United States Patent
Thomas

(10) Patent No.: US 7,188,855 B1
(45) Date of Patent: Mar. 13, 2007

(54) ARTICULATING OXYGEN TANK HOLDER

(76) Inventor: E. Trevor Thomas, 12366 Corporal Cir., Port Charlotte, FL (US) 33953

( * ) Notice: Subject to any disclaimer, the term of this patent is extended or adjusted under 35 U.S.C. 154(b) by 112 days.

(21) Appl. No.: 11/118,174

(22) Filed: Apr. 29, 2005

(51) Int. Cl.
*A47C 7/62* (2006.01)

(52) U.S. Cl. ................................. 280/304.1; 280/288.4

(58) Field of Classification Search ............ 280/304.1, 280/250.1, 288.4, 292; 135/67; D12/133
See application file for complete search history.

(56) References Cited

U.S. PATENT DOCUMENTS

| | | | | | |
|---|---|---|---|---|---|
| 3,970,344 | A | * | 7/1976 | Baumann | 297/188.02 |
| 4,213,648 | A | * | 7/1980 | Steichen | 297/188.2 |
| 4,431,206 | A | * | 2/1984 | Pryor | 280/304.1 |
| 4,506,903 | A | * | 3/1985 | Bowermaster | 280/304.1 |
| 4,696,420 | A | * | 9/1987 | Kulik | 224/275 |
| D305,629 | S | * | 1/1990 | Wood | D12/133 |
| D342,222 | S | * | 12/1993 | Cherry | D12/133 |
| 5,288,001 | A | * | 2/1994 | Locarno | 224/407 |
| 5,340,140 | A | * | 8/1994 | Bynum | 280/304.1 |
| 5,769,440 | A | * | 6/1998 | Jones | 280/204 |
| 6,273,444 | B1 | * | 8/2001 | Power | 280/304.1 |

* cited by examiner

*Primary Examiner*—Tony Winner
(74) *Attorney, Agent, or Firm*—Charles J. Prescott

(57) ABSTRACT

An oxygen tank holder attachable to a reclining seatback-type wheelchair. The holder includes a T-shaped main frame including an elongated upright central member and an upper support arm extending horizontally in either direction from an upper end of the central member. Each end of the upper support arm adapted for slidable or fixed connection to and along the sides of the wheelchair. A lower support bar is connected to, and extends laterally in either direction from a lower end of the central member, each distal end thereof adapted for connection to a lower side frame bar of the wheelchair. Spaced tubular upper and lower oxygen cylinder carriers are connected to the central member for receiving an elongated cylindrical oxygen tank positioned uprightly therein, securing the tank from excessive when the seat back is reclined or the wheelchair transported.

3 Claims, 3 Drawing Sheets

ARTICULATING OXYGEN TANK HOLDER

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to a device for carrying life support devices and more particularly to an oxygen cylinder carrier attachment for a medical transport device, such as a wheelchair.

As is normal during the treatment or transportation of an injured or disabled patient, it is necessary to move the patient to other locations in the hospital for surgery, special tests, etc. To my knowledge, both in the past and present, it is generally the practice to place life support devices such as oxygen cylinders on a bed with a patient or on a wheeled device which is pulled along with the wheelchair while it is being moved. Other procedures and devices have included extra attendants who carry the life support devices and/or means to carry them.

2. Description of Related Art

One such device is shown in U.S. Pat. No. 4,691,397 to Netzer which discloses a life support carrying apparatus which carries the life supporting devices of a bedridden patient that cooperates with the footboard of the bed. The device includes a table-like surface for supporting life support devices.

U.S. Pat. No. 5,259,372 to Gross, et al. discloses an oxygen cylinder carrier apparatus for stretchers. The carrier apparatus includes a flexible, coated material base open at one end with a drawstring closure and adjustable straps adapted to be mounted on the upper framework of the stretcher in unused space just in front of the upper and lower frame members of the stretcher at its head end. The adjustability of the straps allows for use of the apparatus with various models of stretchers.

U.S. Pat. No. 6,213,529 to Kurcz, et al. discloses a carrier for storing and carrying a pair of cylindrical shaped canisters.

BRIEF SUMMARY OF THE INVENTION

This invention is directed to a simple means attachable to a reclining wheelchair for accommodating a patient's oxygen bottle without extra attendants. Firstly, the invention preferably includes a "T" shaped tubular structure having an upright central member with a "T" joint fastened to the upper end thereof and horizontally extending upper support arms fastened at each end of the "T" joint. Elbows are attached in a forwardly oriented position to each of the ends of the upper support arms. A cylindrical glide is attached to each of the elbows in an upright orientation. Two spaced cylinder carriers are fastened to the central member. An elongated transversely extending lower support bar is preferably inserted through aligned holes formed adjacent to a lower end of the lower cylinder carrier. A shaped clamp is mounted on each outer end of the lower support bar for attachment to the outer lower rear frame bars of the wheelchair. The cylinder carriers are fastened to the central member with screws. A set screw is located in one of the cylinder carriers to secure the oxygen tank in place. The set screw may be made of nylon or stainless steel having a base on its end to reduce pressure against the side of the oxygen tank.

It is therefore an object of this invention to provide an oxygen tank holder adapted for attachment to the back of a reclining wheelchair.

Yet another object of this invention is to provide an oxygen tank holder connectable to the back of a reclining wheelchair which will securely maintain the oxygen tank within the holder during periods of seat back recline and wheelchair transport.

Still another object of this invention is to provide an oxygen tank holder which is easily connectable onto the reclining seat back area of an articulating reclining wheelchair without modification to the wheelchair itself.

In accordance with these and other objects which will become apparent hereinafter, the instant invention will now be described with reference to the accompanying drawings.

BRIEF DESCRIPTION OF THE SEVERAL VIEWS OF THE DRAWING(S)

DETAILED DESCRIPTION OF THE INVENTION

Figure 1:
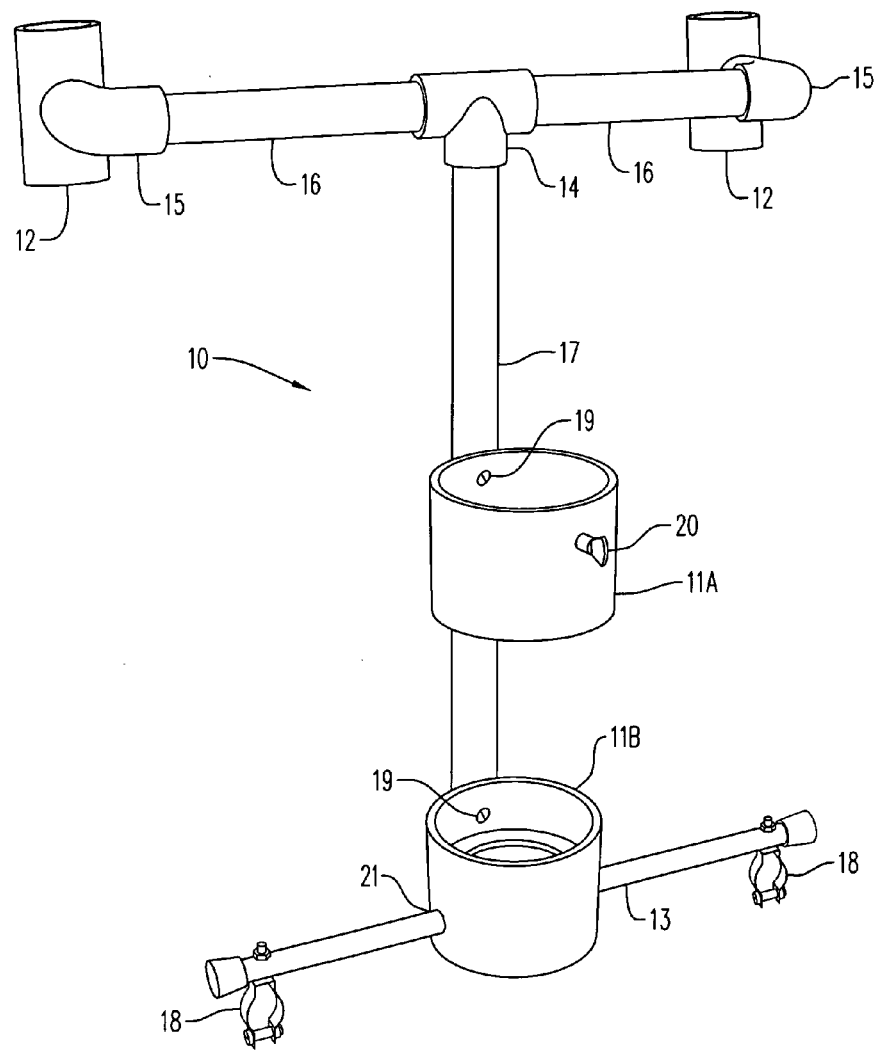
FIG. 1 is a rear perspective view of one embodiment of the present invention.

FIG. 1 shows the oxygen bottle holder 10 of the present invention and preferably includes a "T" shaped tubular structure comprising an elongated tubular upright central member 17 with a "T" joint 14 fastened to the top thereof. Two elongated horizontally disposed upper support arms 16 are fastened and laterally extend from opposite ends of the joint 14. An elbow 15 is fastened at the outer end of each upper support arm 16. A cylinder glide 12 is fastened to each elbow 15 in an upright orientation as shown.

A two-part cylinder carrier formed of tubular carriers 11A and 11B is fastened to the central member 17 with screws 19. Holes 21 are formed transversely aligned through the lower cylinder carrier 11B adjacent the lower end thereof and an elongated lower support bar 13 is slidably or forcibly inserted through the holes 21 and evenly spaced A clamp 18 is mounted on each end of the lower support bar 13 for attachment to the rear frame bars 31 of the wheelchair 30. A thumb screw 20 is inserted in one of the tubular members 11 to hold the tank T (shown in phantom in FIG. 2) secure to comply with safety regulations.

Figure 2:
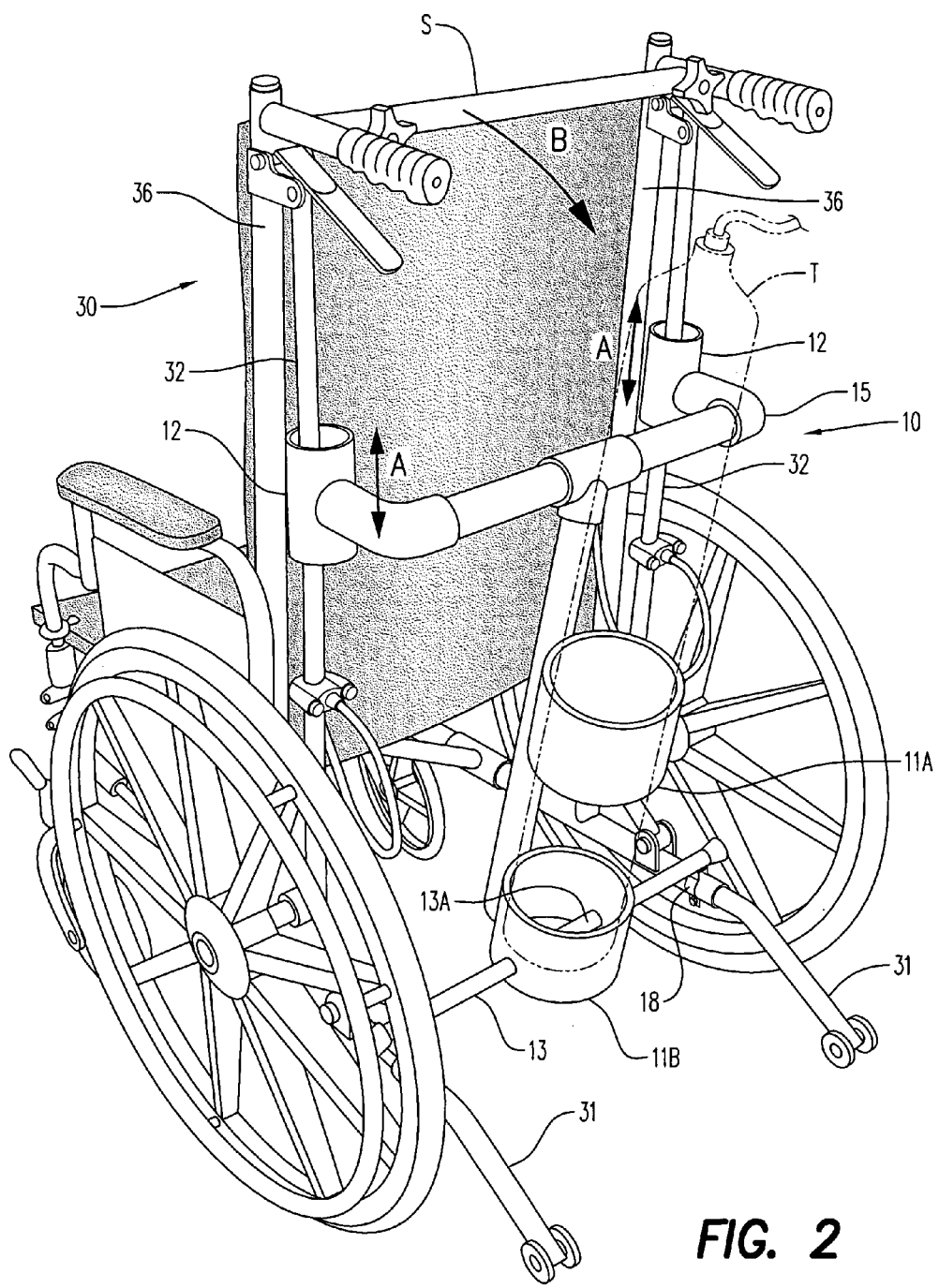
FIG. 2 is a rear perspective view of the invention of FIG. 1 connected to one version of a reclining seat back of a wheelchair.

FIG. 2 is a rear perspective view of the oxygen tank holder 10 mounted behind the reclining seat back S of a reclining wheelchair 30. The holder 10 is installed on the wheelchair 30 by assembling the glides 12 over pneumatic tubular air springs 32. The lower support bar 13 is fastened to rear frame bars 31 with clamps 18. The glides 12 slide up and down the air springs 32 in the direction of arrow A when the seat back S of the wheelchair 30 is reclined in the direction of arrow B.

The oxygen tank holder 10 may be constructed from PCV tubes and the support bar 13 may be constructed from aluminum. The oxygen tank T shown in phantom is then installed in the holder 10 and secured in place by the thumbscrew 20 threadably engaged through the wall of the upper tubular carrier 11A.

Figure 3:
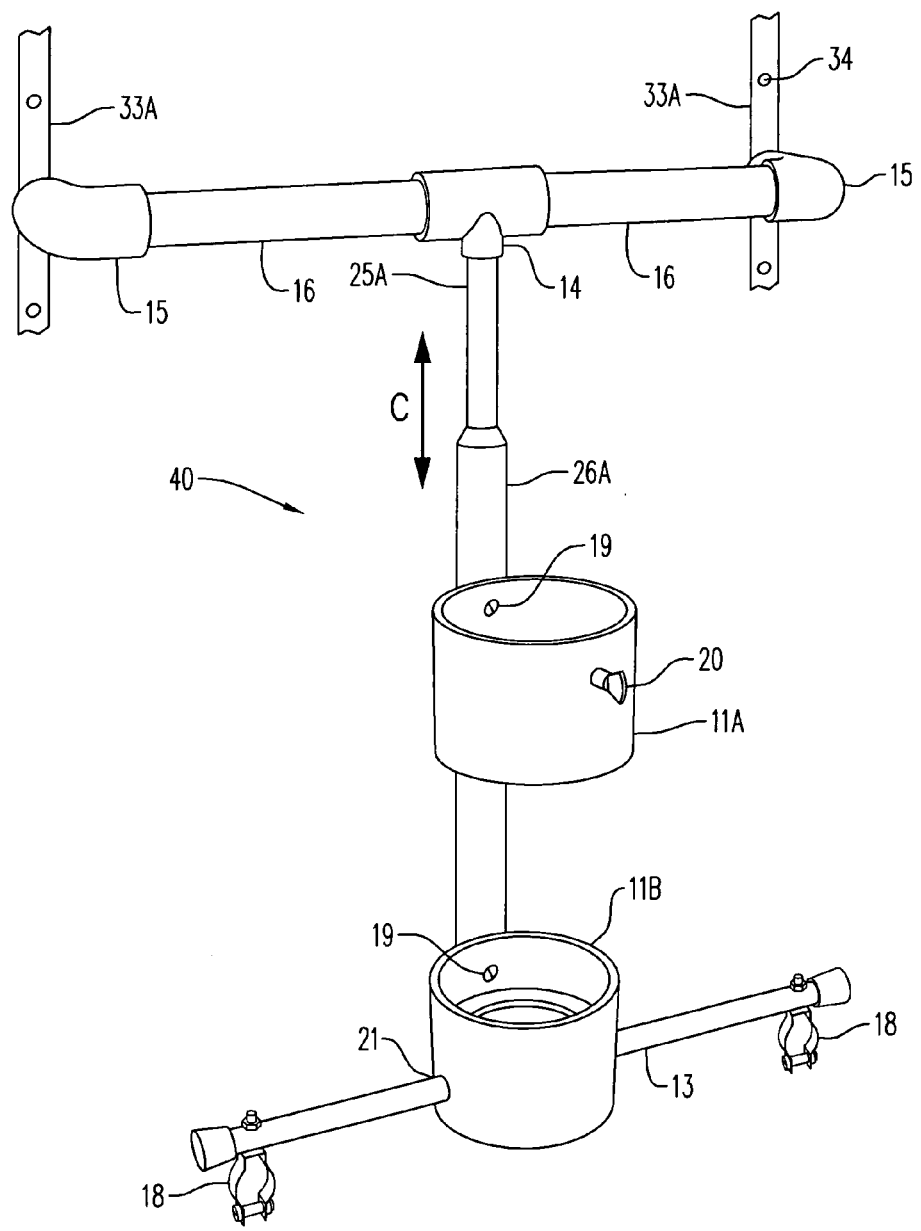
FIG. 3 is a rear perspective view of another embodiment of the invention adapted for another version of a reclining wheelchair.

Referring now to FIG. 3, an alternate embodiment of the oxygen tank holder is there shown generally at numeral 40 and includes a substantial number of the structural features of the embodiment 10 described in FIGS. 1 and 2 and numbered with like numbers. However, this embodiment 40, intended for use with a reclining wheelchair not equipped with the pneumatic air springs 32, is attached directly to the upright tubular side frames 36 of the seat back S. Attachment of the upper support arms 16 at the distal elbows 15 is achieved by elongated straps 33a which are connected by fasteners through mounting holes 34 directly to the upright side frame members 36.

To achieve the shortening of the height of the device 40 as the seat back S is reclined rearwardly in the direction of arrow B in FIG. 2, the two-piece tubular central member 26a/25a of the main frame is made to telescope in length in the direction of arrow C. By this arrangement, the tank T shown in FIG. 2, will be maintained in a stable, substantially upright or slightly tilted orientation within the upper and lower tubular carriers 11A and 11B, respectively, supported vertically on the lower support member 13 as previously described.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

The invention claimed is:

1. An oxygen tank holder for a reclining wheelchair comprising:
   a T-shaped main frame including an elongated upright central member and a laterally extending upper support arm extending substantially horizontally in either direction from an upper end of said central member;
   a distal end of each of said upper support arms adapted for slidable connection to and along an elongated tubular member of the wheelchair which extends along either side of a reclining seat back of the wheelchair;
   an elongated laterally extending lower support bar connected to, and extending substantially horizontally in either direction from a lower end of said central member;
   each distal end of said lower support adapted for connection to an outer rear frame bar of the wheelchair;
   spaced upper and lower tubular carriers connected in substantially coaxial upright alignment to said central member and being adapted to receive and support an elongated cylindrical oxygen tank positioned upright therein;
   whereby the oxygen tank remains stable from excessive movement within, and tilting with, said cylinder carriers as the seat back is reclined.

2. An oxygen tank holder for a reclining wheelchair comprising:
   a T-shaped main frame including an elongated telescoping upright central member and a laterally extending upper support arm extending substantially horizontally in either direction from an upper end of said central member;
   a distal end of each of said upper support arms adapted for fixed connection to and along an elongated tubular member of the wheelchair which extends along either side of a reclining seat back of the wheelchair;
   an elongated laterally extending lower support bar connected to, and extending substantially horizontally in either direction from a lower end of said central member;
   each distal end of said lower support adapted for connection to an outer rear frame bar of the wheelchair;
   upper and lower spaced tubular carriers connected in substantially coaxial upright alignment to said central member and being adapted to receive and support an elongated cylindrical oxygen tank positioned upright therein;
   whereby the oxygen tank remains stable from excessive movement within, and tilting with, said cylinder carriers responsive to telescopic shortening of said central member as the seat back is reclined.

3. An oxygen tank holder for a reclining wheelchair comprising:
   a T-shaped main frame including an elongated upright central member and a laterally extending upper support arm extending substantially horizontally in either direction from an upper end of said central member;
   a distal end of each of said upper support arms adapted for slidable connection to and along an elongated tubular side frame member extending along either side of a reclining seatback of the wheelchair;
   spaced tubular substantially coaxially aligned upper and lower cylinder carriers connected to said central member and being adapted to receive and laterally support an oxygen tank positioned coaxially therein;
   an elongated laterally extending lower support bar connected through transversely aligned holes through a wall of said lower cylinder carrier, and extending substantially horizontally in either direction therefrom whereby the oxygen tank positioned within said cylinder carriers is supported on said lower support bar;
   each distal end of said lower support adapted for connection to an outer rear frame bar of the wheelchair;
   whereby the oxygen tank remains stable from excessive movement within, and tilting with, said cylinder carriers as the seat back is reclined.

* * * * *